United States Patent
Tanaka et al.

(10) Patent No.: US 12,023,172 B2
(45) Date of Patent: Jul. 2, 2024

(54) MUSCULAR RELAXATION MONITORING DEVICE, MUSCULAR RELAXATION MONITORING METHOD AND MUSCULAR RELAXATION MONITORING PROGRAM

(71) Applicant: Nihon Kohden Corporation, Tokorozawa (JP)

(72) Inventors: Rie Tanaka, Tokyo (JP); Kazuya Nagase, Tokyo (JP)

(73) Assignee: Nihon Kohden Corporation, Tokorozawa (JP)

( * ) Notice: Subject to any disclaimer, the term of this patent is extended or adjusted under 35 U.S.C. 154(b) by 281 days.

(21) Appl. No.: 15/381,800

(22) Filed: Dec. 16, 2016

(65) Prior Publication Data
US 2017/0172492 A1 Jun. 22, 2017

(30) Foreign Application Priority Data
Dec. 21, 2015 (JP) ................. 2015-248974

(51) Int. Cl.
*A61B 5/00* (2006.01)
*A61B 5/11* (2006.01)
(Continued)

(52) U.S. Cl.
CPC .......... *A61B 5/4519* (2013.01); *A61B 5/1107* (2013.01); *A61B 5/742* (2013.01);
(Continued)

(58) Field of Classification Search
CPC ....... A61B 5/45; A61B 5/4519; A61B 5/4523; A61B 5/0488; A61B 5/1107; A61B 5/742;
(Continued)

(56) References Cited

U.S. PATENT DOCUMENTS

| | | | |
|---|---|---|---|
| 5,285,781 A * | 2/1994 | Brodard | A61N 1/36034 607/66 |
| 8,401,632 B1 * | 3/2013 | Stone | A61B 5/7221 600/546 |

(Continued)

FOREIGN PATENT DOCUMENTS

| | | |
|---|---|---|
| JP | 4706962 | 6/2011 |
| WO | 2005051201 A1 | 6/2005 |
| WO | 2014059259 A1 | 4/2014 |

OTHER PUBLICATIONS

Ali et al. "Stimulus Frequency in the Detection of Neuromuscular Block in Humans", Brit. J. Anaesth. 1998; 80: 530-541 (Year: 1998).*

(Continued)

*Primary Examiner* — May A Abouelela
*Assistant Examiner* — Anna Roberts
(74) *Attorney, Agent, or Firm* — Dorsey & Whitney LLP (57) ABSTRACT

To provide a muscular relaxation monitoring device, a muscular relaxation monitoring method and a muscular relaxation monitoring program capable of accurately grasping a muscular relaxation state of a subject. An input/output unit obtains a first reaction, a second reaction, a third reaction and a fourth reaction which are the first to fourth stimulation reaction values of four consecutive stimulations of a muscle. A display unit displays a display screen. A control unit generates the display screen in which a display effect of the first reaction and the fourth reaction is different from a display effect of the second reaction and the third reaction.

19 Claims, 7 Drawing Sheets

(51) Int. Cl.
*A61N 1/02* (2006.01)
*A61N 1/36* (2006.01)

(52) U.S. Cl.
CPC ............ *A61B 5/743* (2013.01); *A61B 5/7455* (2013.01); *A61N 1/025* (2013.01); *A61N 1/36003* (2013.01)

(58) Field of Classification Search
CPC ..... A61B 5/743; A61B 5/7445; A61B 5/7455; A61B 5/389; A61N 1/025; A61N 1/36003
See application file for complete search history.

(56) References Cited

U.S. PATENT DOCUMENTS

| | | | |
|---|---|---|---|
| 8,983,613 | B2 | 3/2015 | Kamataki et al. |
| 9,392,953 | B1* | 7/2016 | Gharib ............... A61N 1/36017 |
| 2002/0111559 | A1* | 8/2002 | Kurata ................. A61B 5/0537 600/547 |
| 2004/0254617 | A1 | 12/2004 | Hemmerling et al. |
| 2006/0270943 | A1* | 11/2006 | Kamataki ........... A61B 5/4041 600/554 |
| 2007/0293918 | A1* | 12/2007 | Thompson ......... A61N 1/36021 607/72 |
| 2008/0077192 | A1* | 3/2008 | Harry .................. A61N 1/0484 607/48 |
| 2009/0018610 | A1* | 1/2009 | Gharib .................. A61B 17/02 607/48 |
| 2009/0054804 | A1* | 2/2009 | Gharib ................ A61B 5/7455 600/554 |
| 2009/0222065 | A1* | 9/2009 | Dlugos, Jr. .............. A61B 5/03 607/60 |
| 2010/0016926 | A1* | 1/2010 | Rittman, III ....... A61N 1/36021 607/62 |
| 2011/0004071 | A1* | 1/2011 | Faiola .................. A61B 5/7445 600/300 |
| 2011/0137134 | A1* | 6/2011 | Hemmerling ........ A61B 5/0205 600/301 |
| 2013/0289664 | A1* | 10/2013 | Johanek ............. A61N 1/36185 607/62 |
| 2014/0107524 | A1* | 4/2014 | Brull .................... A61B 5/0488 600/554 |
| 2015/0133824 | A1 | 5/2015 | Atlas et al. |
| 2015/0230749 | A1* | 8/2015 | Gharib ............... A61B 17/0218 600/546 |
| 2015/0351655 | A1* | 12/2015 | Coleman ................ G16H 50/20 600/301 |
| 2015/0366502 | A1* | 12/2015 | Kusik ..................... A61B 5/02 600/301 |
| 2017/0135590 | A1* | 5/2017 | Itagaki ............... G01R 33/4833 |
| 2017/0164875 | A1* | 6/2017 | Durfee ................. A61B 5/1106 |
| 2017/0281946 | A1* | 10/2017 | Katnani ............... A61N 1/0534 |
| 2019/0059808 | A1* | 2/2019 | Ukawa .................. A61B 5/742 |

OTHER PUBLICATIONS

Extended European Search Report dated May 9, 2017 for European application No. 16205007.4.
Office Action dated Mar. 19, 2019 for European application No. 16205007.4.

* cited by examiner

FIG. 5

MUSCULAR RELAXATION MONITORING DEVICE, MUSCULAR RELAXATION MONITORING METHOD AND MUSCULAR RELAXATION MONITORING PROGRAM

CROSS REFERENCE TO RELATED APPLICATION

This application claims priority to Japanese Application No. JP 2015-248974 filed Dec. 21, 2015, which is incorporated herein by reference, in its entirety, for any purpose.

TECHNICAL FIELD

The present invention relates to a muscular relaxation monitoring device, a muscular relaxation monitoring method and a muscular relaxation monitoring program.

DESCRIPTION OF RELATED ART

Train Of Four (TOF) technique can be cited as one of techniques for monitoring a muscular relaxation state of a subject. The TOF technique is a technique of giving muscle stimulations repeatedly at every 15 seconds by taking four continuous stimulations (four consecutive stimulations) performed at intervals of 0.5 seconds as a group. In the TOF technique, the muscular relaxation state is determined by using a ratio (TOP ratio) between the first stimulation and the fourth stimulation in the group of stimulations (four consecutive stimulations). In the case where a muscle relaxant does not work, the TOF ratio will be 100%.

Japanese Patent No. 4706962 (Patent Document 1) discloses a monitor for displaying a muscular relaxation state, which displays plural muscular relaxation parameters including the TOF ratio on the same monitor screen. The monitor for displaying the muscular relaxation state displays a display screen (FIG. 4 and FIG. 5) in which a TOF count is reversely displayed with respect to the TOF ratio.

SUMMARY OF THE INVENTION

As described above, the determination is made by using the first stimulation and the fourth stimulation included in the four consecutive stimulations in the TOF technique. However, a general display device of the TOF technique does not discriminate between the first/fourth stimulations and the second/third stimulations when performing display. There is a problem that it is difficult to accurately grasp the muscular relaxation state of the subject due to the above display mode.

In view of the above, an object of the present: invention is to provide a muscular relaxation monitoring device, a muscular relaxation monitoring method and a muscular relaxation monitoring program capable of accurately grasping the muscular relaxation state of a subject.

According to an embodiment of the present invention, there is provided a muscular relaxation monitoring device including an obtaining unit that obtains a first reaction, a second reaction, a third reaction and a fourth reaction which are the first to fourth stimulation reaction values of four consecutive stimulations of a muscle, a display unit that displays a display screen and a control unit that generates a display screen in which a display effect of the first reaction and the fourth reaction is different from a display effect of the second reaction and the third reaction.

The control unit varies the display effect of the first reaction and the fourth reaction of four consecutive stimulations with respect to a muscle with respect to the display effect of the second reaction and the third reaction. Accordingly, a medical worker can easily focus on the first reaction and the fourth reaction and can grasp the TOF ratio intuitively.

According to the present invention, the muscular relaxation monitoring device, the muscular relaxation monitoring method and the muscular relaxation monitoring program capable of accurately grasping the muscular relaxation state of a subject can be provided.

DETAILED DESCRIPTION

Figure 1:
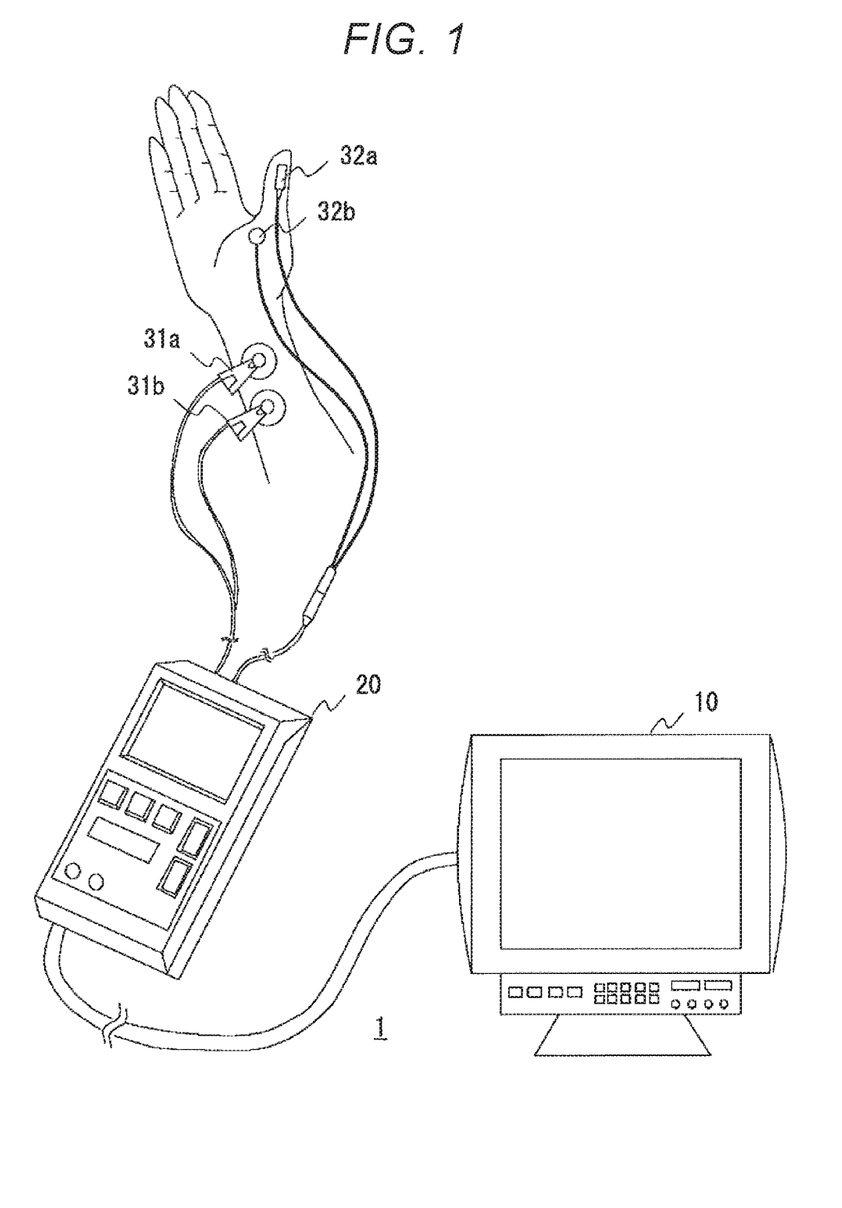
FIG. 1 is a view showing an external structure of a monitoring system according to an embodiment of the present disclosure.

Hereinafter, embodiments of the present invention will be explained with reference to the drawings. FIG. 1 is a view showing an external structure of a monitoring system 1 according to an embodiment of the present disclosure. The monitoring system 1 includes a biological information monitor 10 and an electric stimulation measuring device 20.

The biological information monitor 10 is a so-called bed side monitor, which is an example of the muscular relaxation monitoring device displaying stimulation reactions of four consecutive stimulations of a subject. The biological information monitor 10 is connected to not-shown various electrodes, a cuff and so on, measuring and displaying various biological information parameters (blood pressure, body temperature, electrocardiogram, heart rate, SpO2, respiratory condition, etc.). Stimulation reactions by the TOF technique are inputted into the biological information monitor 10 from the later-described electric stimulation measuring device 20. The biological information monitor 10 displays the inputted stimulation reactions. The details of a display mode by the biological information monitor 10 will be described later with reference to FIG. 3 and else. The biological information monitor 10 may appropriately have other functions (e.g., a defibrillation function) as long as the biological information monitor 10 measures and displays any of biological information parameters (e.g., vital signs). The biological information monitor 10 may also be a transport monitor or a medical telemeter.

The electric stimulation measuring device 20 is a device that may be coupled to the biological information monitor 10 through an electric connector. The electric stimulation measuring device 20 and the biological information monitor 10 may be coupled by wireless instead of wired connection. The electric stimulation measuring device 20 performs muscle stimulation through stimulation electrodes 31a and 31b. The electric stimulation measuring device 20 detects a stimulation reaction through a muscle reaction sensor 32a and a surface temperature sensor 32b. The electric stimulation measuring device 20 may have a simple structure including, for example, buttons and indicators, not limited to the shown configuration including a display.

Figure 2:
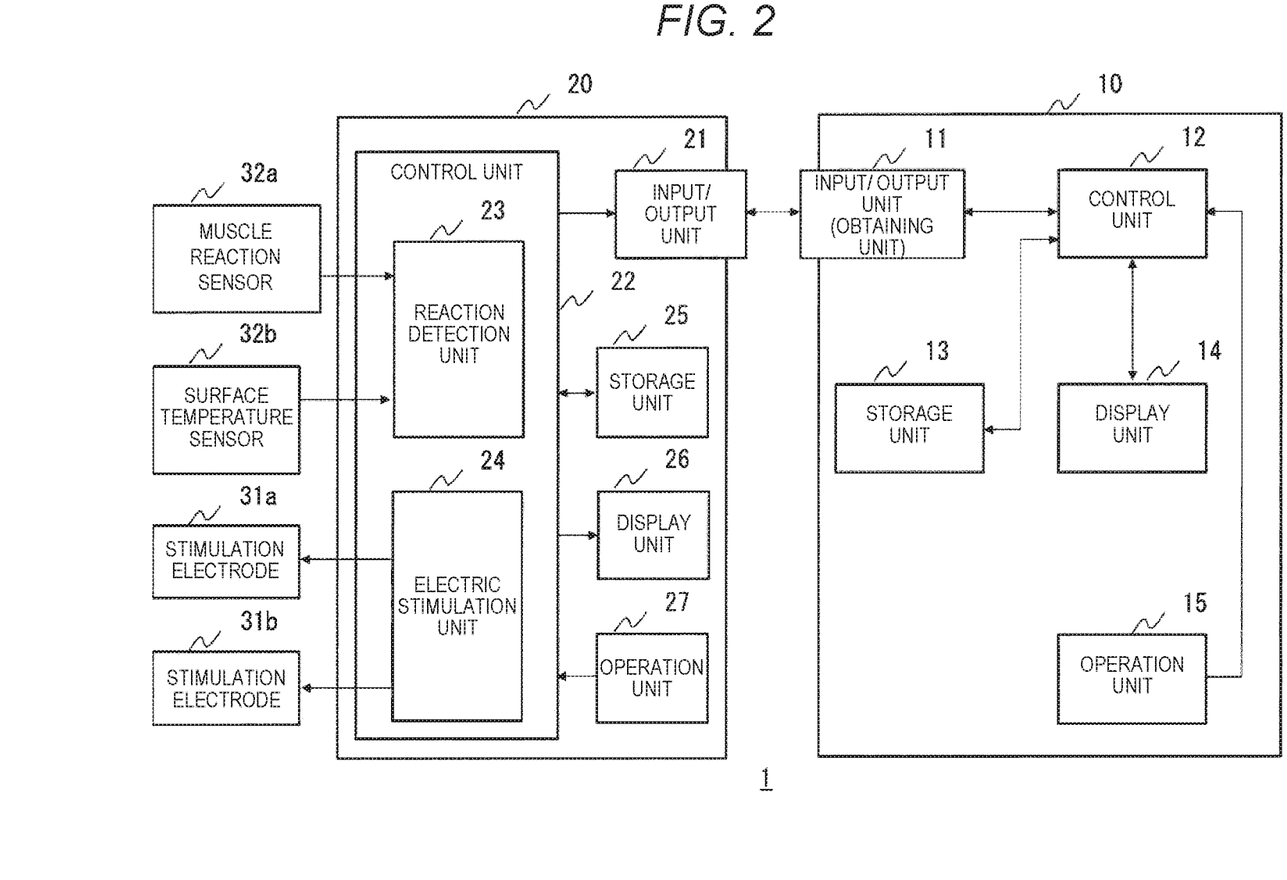
FIG. 2 is a block diagram showing an internal configuration of the monitoring system according to an embodiment of the present disclosure.

Subsequently, the detailed configuration of the monitoring system 1 will be explained with reference to FIG. 2. FIG. 2 is a block diagram showing an internal configuration of the monitoring system 1. The electric stimulation measuring device 20 includes an input/output unit 21, a control unit 22, a storage unit 25, a display unit 26 and an operation unit 27. The control unit 22 includes a reaction detection unit 23 and an electric stimulation unit 24.

The input/output unit 21 performs data transmission/reception with respect to the biological information monitor 10 through a cable line. The input/output unit 21 may be formed of an electric connector and so on. When performing wireless transmission/reception, the input/output unit 21 may be formed of an antenna and so on. The input/output unit 21 transmits stimulation reaction values (first reaction to fourth reaction) of four consecutive stimulations detected by the later-described reaction detection unit 23 to the biological information monitor 10.

The control unit 22 performs various types of controls for the electric stimulation measuring device 20. For example, the control unit 22 controls display of the display unit 26 and writes data into the storage unit 25. At least part of processing of the control unit 22 may be executed by a central processing unit (CPU, not shown) as software.

The electric stimulation unit 24 performs so-called Train Of Four (TOF) stimulation to a muscle of a subject. The TOF stimulation is a stimulation method in which four continuous stimulations (four consecutive stimulations) performed at intervals of 0.5 seconds are set as a group, and the group of stimulations is repeated at every 15 seconds. The electric stimulation unit 24 gives stimulations to the subject through the stimulation electrodes 31a and 31b with a predetermined stimulation strength. The stimulation strength can be set through the later-described operation unit 27 by a medical worker. The stimulation strength is approximately 2 Hz though the strength can be set freely.

The reaction detection unit 23 detects the first to fourth stimulation reaction values included in four consecutive stimulations. The reaction detection unit 23 detects the first to fourth stimulation reaction values of the four consecutive stimulations through the muscle reaction sensor 32a and the surface temperature sensor 32b by the same method as the known muscular relaxation monitoring device. The muscle reaction sensor 32a may be a sensor which detects an acceleration at the time of muscle stimulation and may be a sensor which obtains variation of an electromyography. That is, the muscle reaction sensor 32a is preferably an arbitrary sensor which can obtain stimulation reaction values at the time of TOF stimulation. In the following explanation, the first stimulation reaction value will be referred to as a first reaction, the second stimulation reaction value will be referred to as a second reaction, the third stimulation reaction value will be referred to as a third reaction and the fourth stimulation reaction value will be referred to as a fourth reaction. The reaction detection unit 23 transmits the detected first to fourth reactions to the biological information monitor 10 with stimulation timing (a timestamp when stimulations are given).

The storage unit 25 is a secondary storage which stores various types of data. The storage unit 25 appropriately stores various programs executed by the control unit 25, stimulation strengths of four consecutive stimulations, stimulation reaction values and so on. The storage unit 25 may be a hard disk and so on provided inside the electric stimulation measuring device 20, and may be a device configured to be attached/detached to the electric stimulation measuring device 20 (e.g., a Universal Serial Bus (USB) memory).

The display unit 26 includes a display provided on a casing of the electric stimulation measuring device 20, peripheral circuits thereof and so on. The display unit 26 displays setting values and stimulation reaction values of four consecutive stimulations performed to the subject by the electric stimulation measuring device 20.

The operation unit 27 is an interface for performing various types of inputs with respect to the electric stimulation measuring device 20. For example, the operation unit 27 includes buttons, pulls, knobs and so on provided on the casing of the electric stimulation measuring device 20. The display unit 26 and the operation unit 27 may have an integrated structure (e.g., a touch panel).

Subsequently, an internal configuration of the biological information monitor 10 will be explained. The biological information monitor 10 includes an input/output unit (obtaining unit) 11, a control unit 12, a storage unit 13, a display unit 14 and an operation unit 15. The biological information monitor 10 appropriately includes a speaker and a power supply device, though not shown. The biological information monitor 10 also obtains a biological signal by connecting to not-shown various types of electrodes, a cuff, a mask, a probe and so on.

The input/output unit 11 (obtaining unit) is connected to the electric stimulation measuring device 20 and receives the stimulation strength, stimulation reaction values and so on of the four consecutive stimulations from the electric stimulation measuring device 20. That is, the input/output unit 11 is operated as an obtaining unit that obtains the stimulation strength and the stimulation reaction values (first reaction, second reaction, third reaction and fourth reaction) of the four consecutive stimulations. The input/output unit 11 may be coupled to the electric stimulation measuring device 20 by a cable (wired connection), or by the wireless communication function. The input/output unit 11 may also perform data transmission/reception with respect to a central monitor (not shown) and so on.

The storage unit 13 is a secondary storage which stores various types of data. The storage unit 13 may be a hard disk and so on provided inside the biological information monitor 10, and may be a device configured to be detachable to the biological information monitor 10.

The display unit 14 includes a display of the biological information monitor 10 and peripheral circuits thereof and so on, displaying a later-described display screen. The display screen is generated by the control unit 12. The operation unit 15 includes buttons, pulls, knobs and so on provided on the casing of the biological information monitor 10. The display unit 14 and the operation unit 15 may have an integrated structure (e.g., a touch panel).

The control unit 12 performs various types of controls for the biological information monitor 10. For example, the control unit 12 controls displaying by the display unit 14 and writes data into the storage unit 13. The control unit 12 analyzes a biological signal obtained from an electrode (not shown) and so on, causing an alarm to beep when an abnormality is detected. At least part of processing of the control unit 12 may be implemented as software to be executed by a central processing unit (CPU, not shown).

The control unit 12 generates a display screen in which a display effect of the first reaction and the forth reaction is different from a display effect of the second reaction and the third reaction in the four consecutive stimulations. The control unit 12 also displays a history of stimulation reaction values of the four consecutive stimulations on the display screen. A detailed screen example generated by the control unit 12 will be explained with reference to FIG. 3.

Figure 3:
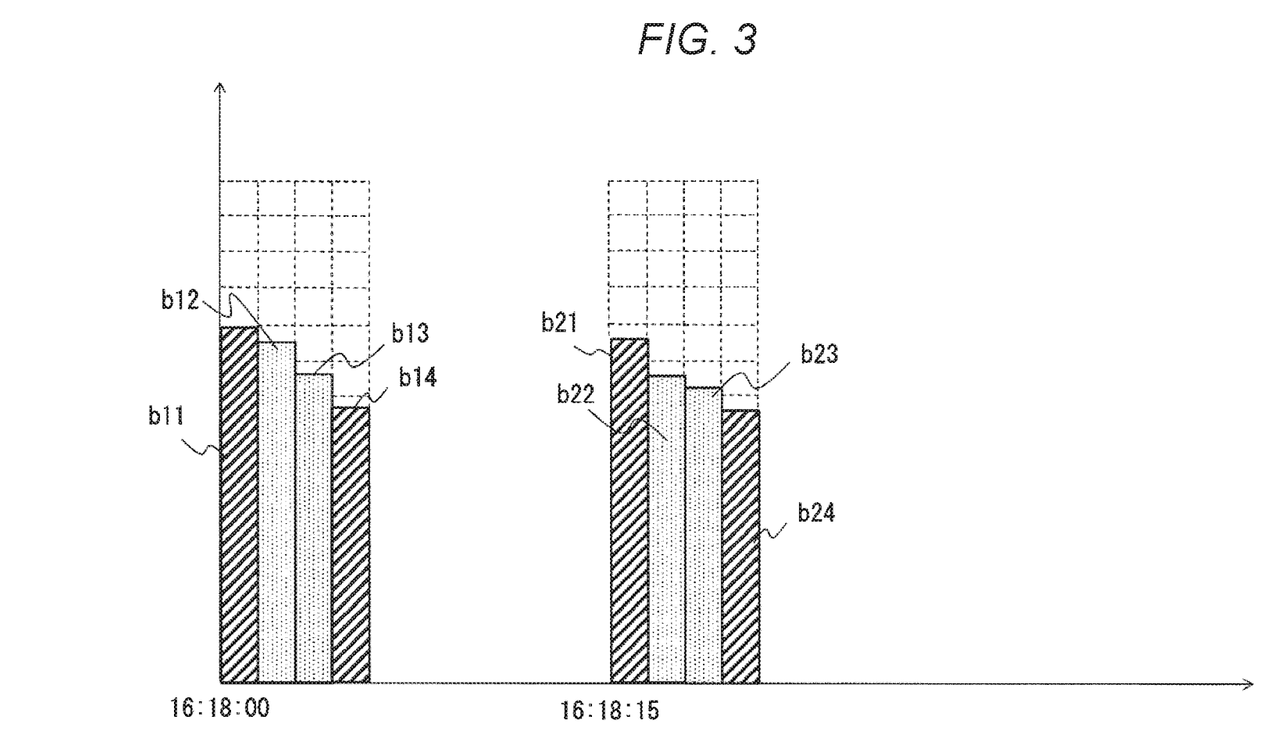
FIG. 3 is a view showing an example of a display screen of a biological information monitor according to an embodiment of the present disclosure.

FIG. 3 is a view showing the first example of the display screen generated by the control unit 12. The control unit 12 displays a chart in which the horizontal axis (first axis) represents time and the vertical axis (second axis) represents stimulation reaction values. The chart in which the horizontal axis (first axis) represents stimulation reaction values and the vertical axis (second axis) represents time does not matter. The control unit 12 displays the first to fourth reactions of the four consecutive stimulations on the chart in a form of bars. In the example, the control unit 12 displays stimulation reaction values (b21 to b24) of four consecutive stimulations started from 16:18:15 (namely, the latest four consecutive stimulations). The control unit 12 preferably represents the history of stimulation reaction values (b11 to b14) of four consecutive stimulations together in the form of bars as illustrated in FIG. 3.

As illustrated in FIG. 3, the control unit 12 generates the display screen in which the display effect of bars indicating the first reaction and the forth reaction is different from the display effect of bars indicating the second reaction and the third reaction. In the example of FIG. 3, the control unit 12 displays a pattern of bars (b11, b21) indicating the first reaction and bars (b14, b24) indicating the fourth reaction as hatching of slanting lines. On the other hand, the control unit 12 displays a pattern of bars (b12, b22) indicating the second reaction and bars (b13, b23) indicating the third reaction as hatching of dots.

To use different patterns between the both as illustrated in FIG. 3 is merely an example. The control unit 12 may distinguish between bars indicating the first reaction and the fourth reaction and bars indicating the second reaction and third reaction by the difference of various display effects (for example, color, illuminance, luminance, brightness, luminous intensity and so on).

Although the control unit 12 represents the first to fourth reactions by bars on the chart in the example shown in FIG. 3, the present invention is not always limited to the example. For example, the control unit 12 may generate a display screen in which the first to fourth reactions are expressed by numeric values. Also in this case, the control unit 12 distinguish between the first and fourth reactions and the second and third reactions by displaying numeral values in a large size or changing the color. That is, the control unit 12 preferably performs display by visually distinguishing between the first and fourth reactions and the second and third reactions. In other words, it is preferable that the control unit 12 causes the display effect of the first and fourth reactions to be different from the display effect of the second and third reactions.

Subsequently, advantages of the biological information monitor 10 (muscular relaxation monitoring device) according to the embodiment will be explained. As described above, the control unit 12 causes the display effect of the first reaction and the fourth reaction of four consecutive stimulations with respect to a muscle to be different from the display effect of the second reaction and the third reaction (FIG. 3). According to the display effects, the medical worker can easily focus on the first reaction and the forth reaction and can grasp the TOF ratio intuitively. In particular, when performing display with the bars as shown in FIG. 3, the medical worker can visually grasp the TOF ratio.

The control unit 12 displays not only stimulation reaction values of the latest four consecutive stimulations but also the history of stimulation reaction values of the four consecutive stimulations. For example, the control unit 12 displays not only the stimulation reaction values (b21 to b24) of the latest four consecutive stimulations (from 16:18:15) but also the stimulation reaction values (b11 to b14) of the past four consecutive stimulations (from 16:18:00) in the example of FIG. 3. Accordingly, the medical worker can easily grasp how the TOE ratio changes. The control unit 12 may display only the latest four consecutive stimulations in the case where the medical worker desires to focus on the latest TOF ratio.

Though the display screen shown in FIG. 3 is a basic structure, various modifications may occur. Hereinafter, a modification example of the display screen will be explained.

Modification Example 1

In a first modification example, the timing of next four consecutive stimulations can be grasped as well as the current time can be grasped. Hereinafter, the first modification example will be explained with reference to FIG. 4.

The control unit 12 generates the display screen on which respective reactions (b11 to b14, b21 to b24) of the latest and the past four consecutive stimulations are displayed in the same manner as the display screen of FIG. 3. Additionally, the control unit 12 generates a display screen on which information related to the timing of next four consecutive stimulations is displayed. In the example, the control unit 12 displays the stimulation timing of next four consecutive stimulations by time (16:18:30) and bars displayed by dotted lines (b31 to b34). The display method of the next stimulation timing is not limited to the expression of FIG. 4 but various expressions for example, display using figures such as circles and squares and so on) can be used. Alternatively, either the time or the bars (b31 to b34) may be displayed in FIG. 3. The control unit 12 may display a character string indicating the time on the outside of the chart without displaying the stimulation timing of next four consecutive stimulations on the chart.

The control unit 12 may further express the current time by a progress bar "p1". The progress bar "p1" extends in the right direction (namely, a direction parallel to the time axis (first axis)) in FIG. 4 with the lapse of time. The control unit 12 displays the progress bar "p1" on the time axis in FIG. 4, however, the present invention is not limited to this expression. The progress bar "p1" may be arranged, for example, to extend in parallel to the time axis at an upper portion of the display screen.

As the next stimulation timing (time or bars b31 to b34) and the progress bar "p1" are displayed (FIG. 4), the subject and the medical worker can easily grasp at what timing next four consecutive stimulations are performed.

Modification Example 2

In a second modification example, the TOF ratios (ratios between the first reactions and the fourth reactions) of respective times of four consecutive stimulations are displayed also in numeric values. The details will be explained below with reference to FIG. 5.

Figure 4:
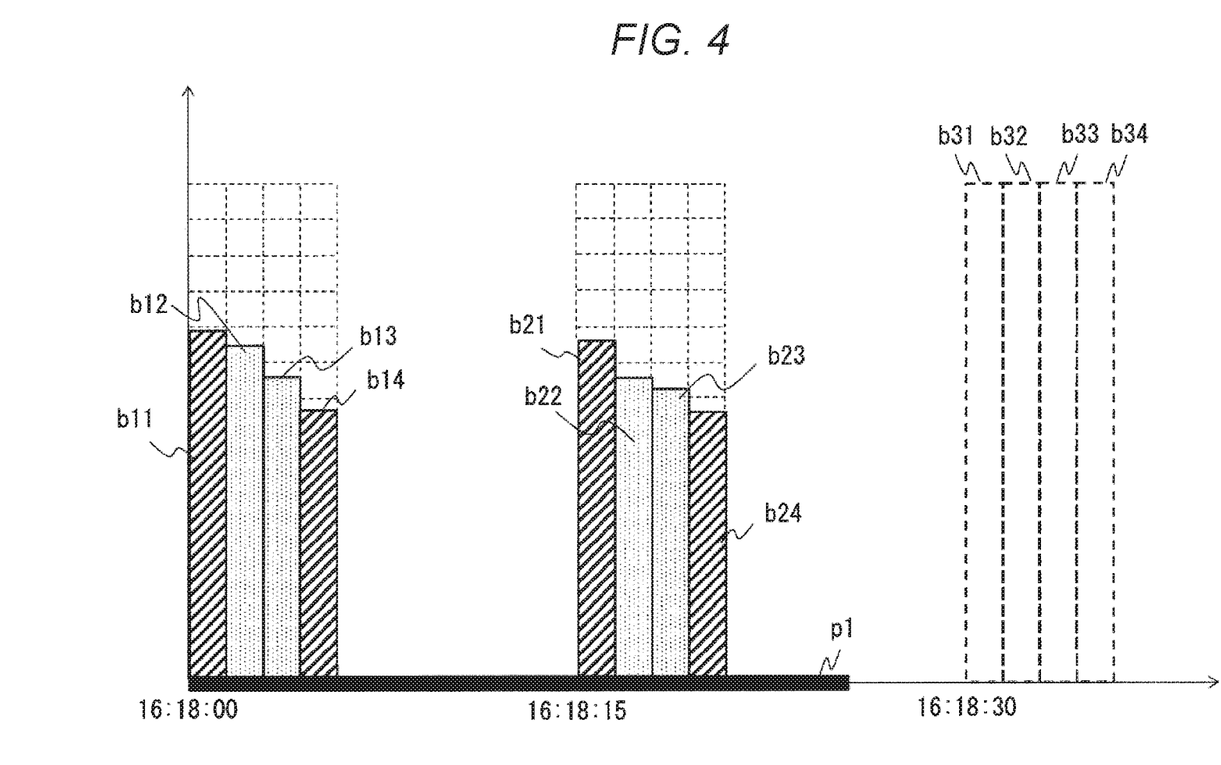
FIG. 4 is a view showing an example of a display screen of the biological information monitor according to an embodiment of the present disclosure.

The TOF ratio is calculated by (the fourth reaction/the first reaction). The control unit 12 calculates the TOF ratio at each time of the four consecutive stimulations. Then, the control unit 12 displays the TOF ratios with the above display control (FIG. 3, FIG. 4).

Figure 5:
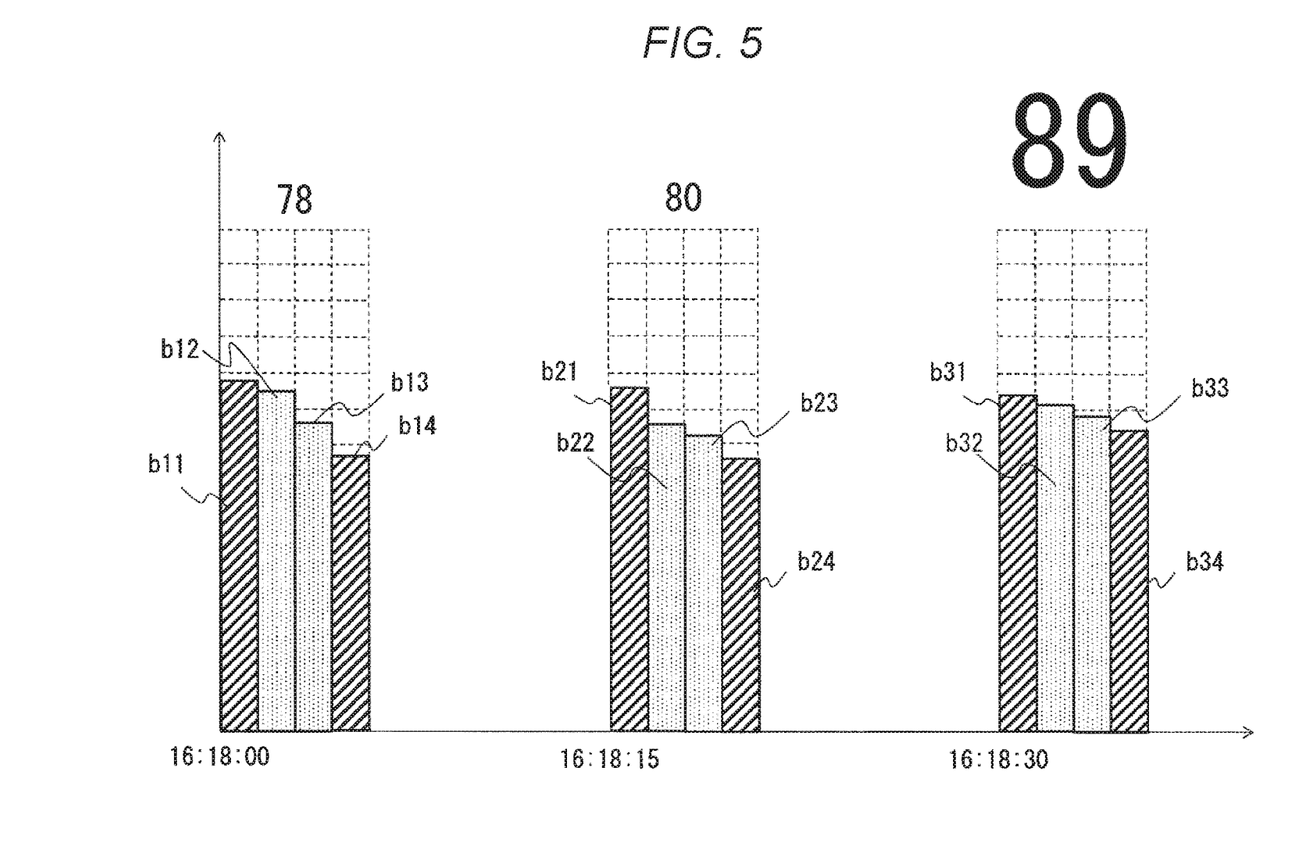
FIG. 5 is a view showing an example of a display screen of the biological information monitor according to an embodiment of the present disclosure.

For example, the control unit 12 calculates a TOF ratio of four consecutive stimulations started from 16:18:00 as 78%, and displays the TOF ratio (78%) near the bars (b11 to b14) by a numeric value. Similarly, the control unit 12 displays a TOE ratio (80%) of four consecutive stimulations started from 16:18:15 near the bars (b21 to b24) by a numeric value.

The control unit 12 also calculates a TOF ratio of the latest four consecutive stimulations (four consecutive stimulations started from 16:18:30) as 89%, and displays the TOE ratio (89%) near the bars (b31 to b34) by a numeric value. Here, it is preferable that the control unit 12 makes the display effect in displaying the numeral value of the latest TOF ratio different from the display effect in displaying the numeral value of the past TOF ratio. In the example of FIG. 5, the latest TOF ratio (89%) is displayed in a larger size than the past TOF ratios (78%, 80%). The control unit 12 may make the latest TOP ratio conspicuous by changing color, luminance, brightness, chroma and so on in the display of the numeric value of the latest TOP ratio from those of the past TOF ratios.

As described above, the control unit 12 displays the TOF ratios by numeric values in addition to the expression of stimulation reaction values (first reaction to fourth reaction) expressed by bars. Doctors and so on can easily grasp accurate numeric values of the TOP ratios and the transition of TOF ratios by referring to the display screen (FIG. 5). Furthermore, doctors and so on can easily grasp the current TOF ratio by displaying the latest TOF ratio in an emphasized manner.

Modification Example 3

In a modification example 3, the state that the muscle stimulation is currently performed is notified by animation display. The details will be explained below with reference to FIG. 6 and FIG. 7. The following explanation will be made based on Modification Example 1 (the example in which the progress bar "p1" and information of the timing of next four consecutive stimulations are displayed).

Figure 6A:
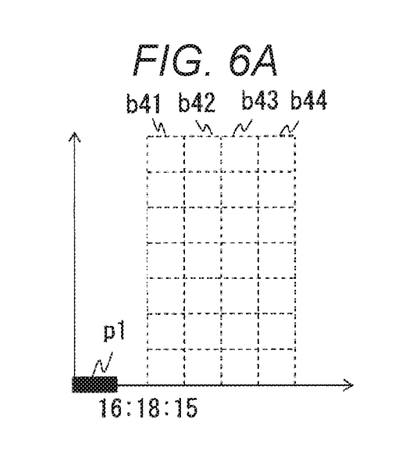
FIGS. 6A to 6F are views showing an example of a display screen of the biological information monitor according to an embodiment of the present disclosure.

FIG. 6A is a conceptual diagram showing a display screen to be displayed before four consecutive stimulations from 16:18:15 is started. The control unit 12 generates a display screen on which time (16:18:15) indicating the next stimulation timing and bars (b41 to b44) are displayed in the same manner as Modification Example 1. The control unit 12 displays the progress bar "p1" indicating the current time.

Figure 6B:
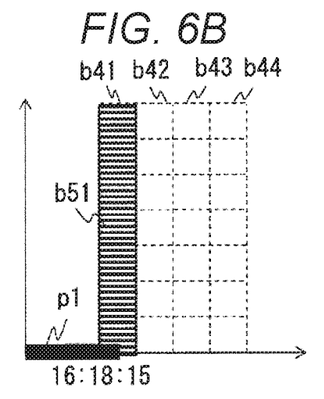

FIG. 6B is a conceptual diagram showing a display screen to be displayed during the first stimulation of the four consecutive stimulations started from 16:18:15. The control unit 12 displays a bar b51 indicating that the stimulation is currently performed (also referred to as a stimulation bar) at a position (b41) corresponding to the first stimulation timing during the execution of the first stimulation of the four consecutive stimulations. It is preferable that the control unit 12 displays the bar b51 so that the height thereof reaches the maximum value (or a value close to the maximum value (for example, 90% or more of the maximum value)) of stimulation reaction values as shown in FIG. 6B for clearly demonstrating that the stimulation is currently performed (the same applies to cases of FIGS. 6C to 6E below).

Figure 6C:
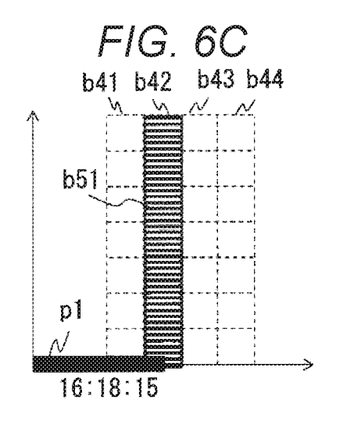

FIG. 6C is a conceptual diagram showing a display screen to be displayed during the second stimulation of the four consecutive stimulations started from 16:18:15. The control unit 12 displays the bar b51 indicating that the stimulation is currently performed at a position (b42) corresponding to the second stimulation timing during the execution of the second stimulation of the four consecutive stimulations. The control unit 12 does not display the bar at the position (b41) corresponding to the first stimulation timing.

Figure 6D:
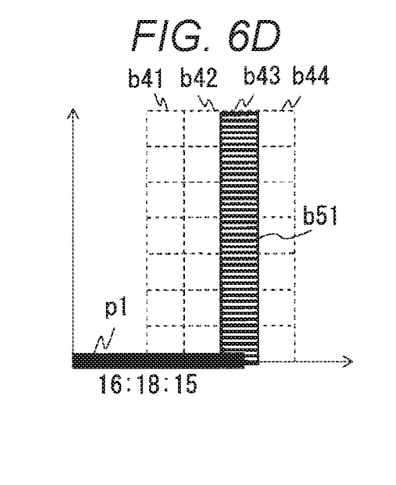
Figure 6E:
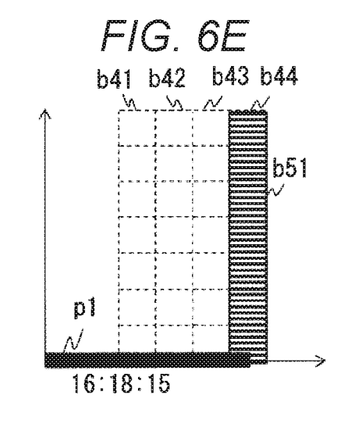

The control unit 12 also performs the same display control as the case of FIG. 6C in the execution of the third and fourth stimulations of the four consecutive stimulations (FIGS. 6D and FIG. 6E).

Figure 6F:
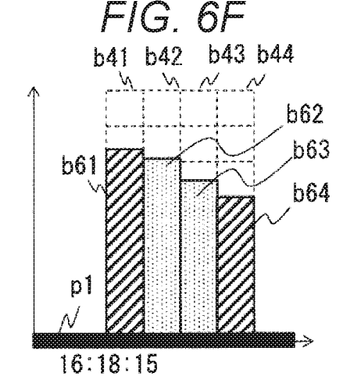

The control unit 12 displays the first to fourth reactions detected by the reaction detection unit 23 by bars (b61 to b64) after completing the four consecutive stimulations. It is preferable that the display effect (for example, a color or a pattern) of the bar b51 indicating that the stimulation is currently performed is different from display effects of bars (b61 to b64) indicating the first to fourth reactions as shown in the drawing. Accordingly, the medical worker can easily grasp whether the stimulation is currently performed or whether the stimulation reaction values are displayed according to the display effect.

As described above, the control unit 12 displays the bar b51 indicating that the stimulation is currently performed at positions (above b41 to b44) corresponding to the stimulation timing of four consecutive stimulations on the chart during the four consecutive stimulations. The control unit 12 may display messages "four consecutive stimulations (first) are now executed", "four consecutive stimulations (second) are now executed, "four consecutive stimulations (third) are now executed" and "four consecutive stimulations (fourth) are now executed" on the outside of the chart instead of displaying that the stimulation is currently performed on the chart. That is, the control unit 12 is enough to generate the display screen on which information indicating that four consecutive stimulations are currently performed is displayed.

It is also possible to make animation in which the bar 51 rises from a height "0" to the vicinity of the maximum value and falls from the vicinity of the maximum value during electric stimulations. FIG. 7 is a view showing the concept of the animation.

Figure 7A:
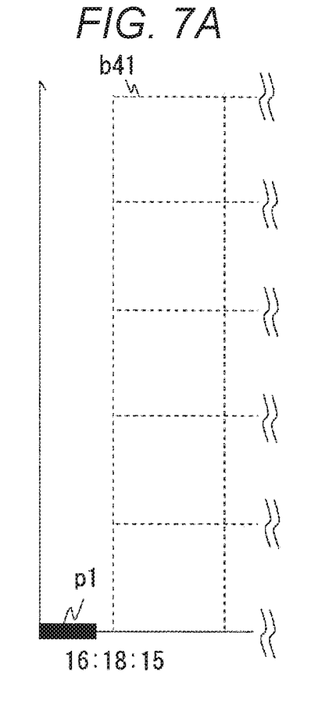
FIGS. 7A to 7D are views showing an example of a display screen of the biological information monitor according to an embodiment of the present disclosure.

FIG. 7A is a view showing a state before four consecutive stimulations are started. The progress bar "p1" and b41 indicating the next stimulation timing are displayed.

Figure 7B:
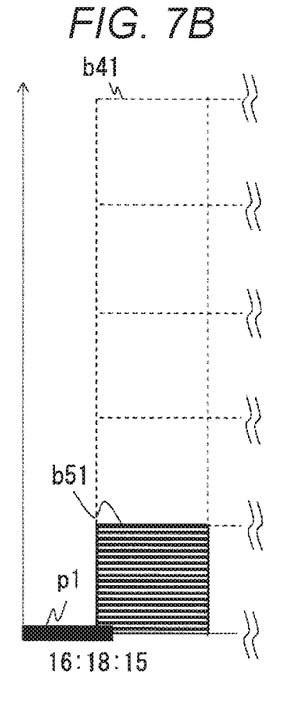

FIG. 7B is a view showing a state just after the first stimulation of four consecutive stimulations is started. The control unit 12 displays animation in which the height of the bar b51 is gradually increased from "0" after the stimulation is started.

Figure 7C:
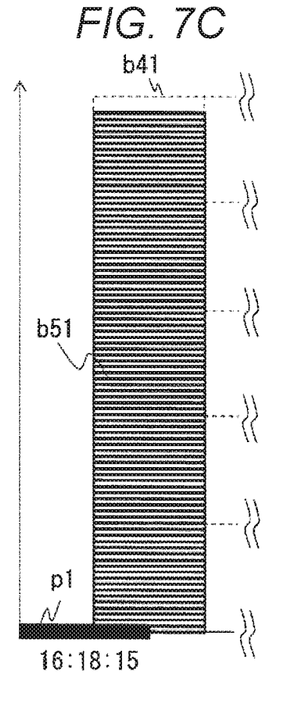

FIG. 7C is a view showing a state during the first stimulation of the four consecutive stimulations (a state in a middle of the stimulation from the beginning to the end). The control unit 12 displays animation in which the height of the bar b51 is gradually increased from the state of FIG. 7B to the vicinity of the maximum value of the stimulation.

Figure 7D:
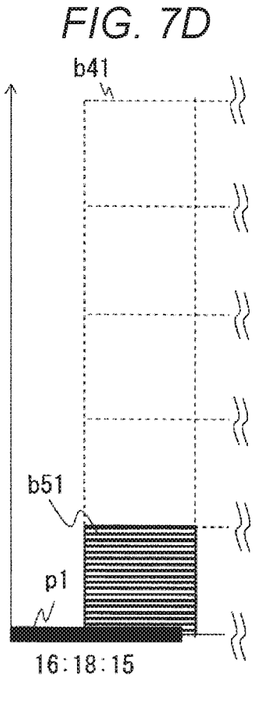

FIG. 7D is a view showing a state just before the end of the first stimulation of the four consecutive stimulations. The control unit 12 displays animation in which the height of the bar b51 is gradually reduced from the state of FIG. 7C. Then, the control unit 12 performs display so that the height of the bar b51 becomes "0" at the end of the stimulation.

The user (medical worker) can intuitively grasp the execution of the stimulation by changing the height of the bar b51 to be decreased after being increased during the start to the end of the stimulation.

FIGS. 6A to 6F and FIGS. 7A to 7D are merely examples of expressions, and the display of the progress bar "p1" and information related to the next stimulation timing (time and the bars b41 to b44) is not necessary in the modification example.

The invention made by the present inventors has been specifically explained based on the embodiments, however, the present invention is not limited to the above embodiments, and various alterations naturally may occur within a scope not departing from the gist thereof.

For example, the general TOF stimulation (intervals of 15 seconds, 2 Hz) is assumed in the above explanation, however, the above biological information monitor 10 may be applied to a slow TOF stimulation (intervals of 1 to 60 minutes, 2 Hz).

In the above explanation, the biological information monitor 10 operates as a muscular relaxation monitoring device which displays stimulation reactions of four consecutive stimulations, however, the present invention is not limited to the above information monitor 10. For example, a central monitor, which receives information of stimulation reactions of four consecutive stimulations from the bedside monitor, may perform display control similar to that of the above biological information monitor 10 (FIG. 3 to FIG. 7D).

Furthermore, the electric stimulation measuring device 20 may perform display similar to that of the above biological information monitor 10 (for example, FIG. 3 and so on). In this case, the reaction detection unit 23 operates as an obtaining unit that obtains the first to fourth reactions as stimulation reaction values of four consecutive stimulations. The control unit 22 may perform the same display control as the above control unit 12 and may display the generated display screen on the display unit 26.

At least part of processing of the above control unit 12 can be implemented as a computer program (muscular relaxation monitoring program) executed inside the biological information monitor 10 (muscular relaxation monitoring device).

Here, the program can be stored by using various types of non-transitory computer readable media to be supplied to a computer. The non-transitory computer readable media include various types of tangible storage media. As examples of non-transitory computer readable media, magnetic recording media (for example, a flexible disk, a magnetic tape and a hard disk drive), magneto-optical recording media (for example, a magneto-optical disk), a CD-ROM (Read Only Memory), a CD-R, a CD-R/W, semiconductor memories (for example, a mask ROM, a PROM (Programmable ROM)), an EPROM (Erasable PROM), a flash ROM and a RAM (Random Access Memory) are included. The program may also be supplied to the computer by various types of transitory computer readable media. Examples of transitory computer recordable media include an electric signal, an optical signal and an electromagnetic wave. The transitory computer recordable media can supply the program to the computer through a wired communication path such as an electric wire or an optical fiber or through a wireless communication path.

What is claimed is:

1. A muscular relaxation monitoring device comprising:
an obtaining unit configured to obtain a first reaction, a second reaction, a third reaction and a fourth reaction which are the first to fourth stimulation reaction values of four consecutive stimulations of a muscle, respectively;
a display unit configured to display a display screen; and
a control unit configured to generate the display screen,
wherein a display effect of the first reaction and the fourth reaction is different from a display effect of the second reaction and the third reaction,
wherein the control unit is configured to display a chart,
wherein a first axis represents time and a second axis represents stimulation reaction values on the display screen, and the control unit is further configured to display the latest first to fourth reactions on the chart in a form of bars, wherein each of the bars is representative of a corresponding stimulation reaction value,
wherein the control unit is configured to display a history of stimulation reaction values of four consecutive stimulations on the chart in a form of bars, and
wherein the control unit is further configured to display a stimulation bar indicating solely the stimulation currently performed, and the control unit is configured to not display stimulation bars indicating stimulations other than the stimulation currently performed, the stimulation bar displayed at a position corresponding to a stimulation timing of four consecutive stimulations on the chart during execution of stimulations of respective times included in four consecutive stimulations.

2. The muscular relaxation monitoring device according to claim 1,
wherein the control unit is configured to display information of a stimulation timing of next four consecutive stimulations on the display screen.

3. The muscular relaxation monitoring device according to claim 1,
wherein the control unit is configured to display a stimulation timing of next four consecutive stimulations on the chart, and further configured to display a current time by a progress bar extending in parallel to the first axis of the chart.

4. The muscular relaxation monitoring device according to claim 1,
wherein the control unit is configured to display a ratio between the first reaction and the fourth reaction in a numeric value.

5. The muscular relaxation monitoring device according to claim 4,
wherein a display effect of the latest ratio between the first reaction and the fourth reaction expressed by a numeric value is different from a display effect of a past ratio between the first reaction and the fourth reaction expressed by a numeric value.

6. The muscular relaxation monitoring device according to claim 1,
wherein the control unit is configured to reduce a height of the stimulation bar, after increasing the height during a period from a start to an end of the stimulation.

7. The muscular relaxation monitoring device according to claim 1, wherein the fourth reaction is a last reaction.

8. The muscular relaxation monitoring device according to claim 1, wherein the control unit is further configured to display stimulation bars corresponding to the four consecutive stimulations on the chart following the execution of stimulations.

9. The muscular relaxation monitoring device according to claim 1, wherein the control unit is further configured to display an animation of the stimulation bar in which a height of the stimulation bar is gradually increased from an initial value after the stimulation is started to a vicinity of a maximum value of the stimulation and the height of the stimulation bar is gradually reduced from the vicinity of the maximum value of the stimulation to the initial value at an end of the stimulation.

10. A muscular relaxation monitoring method comprising:
obtaining a first reaction, a second reaction, a third reaction and a fourth reaction which are the first to fourth stimulation reaction values of four consecutive stimulations of a muscle;
generating a display screen, and
displaying a chart,
wherein a display effect of the first reaction and the fourth reaction is different from a display effect of the second reaction and the third reaction,
wherein a first axis represents time and a second axis represents stimulation reaction values on the display screen,
wherein the latest first to fourth reactions are displayed on the chart in a form of bars, wherein each of the bars is representative of a corresponding stimulation reaction value,
wherein the display screen is configured to display a history of stimulation reaction values of four consecutive stimulations on the chart in a form of bars, and
wherein the display screen is further configured to display a stimulation bar indicating solely the stimulation currently performed and not display stimulation bars indicating stimulations other than the stimulation currently performed, the stimulation bar displayed at a position corresponding to a stimulation timing of four consecutive stimulations on the chart during execution of stimulations of respective times included in four consecutive stimulations.

11. The method of claim 10, wherein the display screen comprises a bar chart including the first to the fourth reactions in a form of bars, the method further comprising:
displaying a stimulation timing of next four consecutive stimulations on the display screen, and
displaying a progress bar indicative of a current time by extending in parallel to the first axis of the chart.

12. The method of claim 10, further comprising:
increasing a height of the stimulus bar during a period from a start to an end of the stimulation; and
reducing a height of the stimulation bar, after the end time of the stimulation.

13. The muscular relaxation monitoring method according to claim 10, wherein the fourth reaction is a last reaction.

14. The muscular relaxation monitoring method according to claim 10, wherein the display screen is further configured to display stimulation bars corresponding to the four consecutive stimulations on the chart following the execution of stimulations.

15. The method according to claim 10, wherein the display screen is further configured to display an animation of the stimulation bar in which a height of the stimulation bar is gradually increased from an initial value after the stimulation is started to a vicinity of a maximum value of the stimulation and the height of the stimulation bar is gradually reduced from the vicinity of the maximum value of the stimulation to the initial value at an end of the stimulation.

16. A non-transitory computer-readable storage medium having stored thereon computer-executable instructions of a muscular relaxation monitoring program that, in response to execution, cause a computer to perform operations, comprising:
obtaining a first reaction, a second reaction, a third reaction and a fourth reaction which are the first to fourth stimulation reaction values of four consecutive stimulations of a muscle, respectively;
generating a display screen wherein a display effect of the first reaction and the fourth reaction is different from a display effect of the second reaction and the third reaction,
displaying a chart, wherein a first axis represents time and a second axis represents stimulation reaction values on the display screen,
displaying the latest first to fourth reactions on the chart in a form of bars, wherein each of the bars is representative of a corresponding stimulation reaction value,
displaying a history of stimulation reaction values of four consecutive stimulations on the chart in a form of bars; and
displaying a stimulation bar indicating solely the stimulation currently performed and not displaying stimulation bars indicating stimulations other than the stimulation currently performed, wherein the stimulation bar is displayed at a position corresponding to a stimulation timing of four consecutive stimulations on the chart during execution of stimulations of respective times included in four consecutive stimulations.

17. The non-transitory computer-readable storage medium having stored thereon computer-executable instructions of a muscular relaxation monitoring program that, in response to execution, cause a computer to perform operations according to claim 16, wherein the fourth reaction is a last reaction.

18. The non-transitory computer-readable storage medium having stored thereon computer-executable instructions of a muscular relaxation monitoring program that, in response to execution, cause a computer to perform operations according to claim 16, further comprising: displaying stimulation bars corresponding to the four consecutive stimulations on the chart following the execution of stimulations.

19. The non-transitory computer-readable storage medium having stored thereon computer-executable instructions of a muscular relaxation monitoring program that, in response to execution, cause a computer to perform operations according to claim 16, further comprising displaying an animation of the stimulation bar in which a height of the stimulation bar is gradually increased from an initial value after the stimulation is started to a vicinity of a maximum value of the stimulation and the height of the stimulation bar is gradually reduced from the vicinity of the maximum value of the stimulation to the initial value at an end of the stimulation.

* * * * *